US007498595B2

(12) United States Patent
Chen

(10) Patent No.: US 7,498,595 B2
(45) Date of Patent: Mar. 3, 2009

(54) POSITRON RADIOACTIVE DRUG RADIATION SHIELDING DEVICE

(75) Inventor: Chi-Kuang Chen, Taipei (TW)

(73) Assignee: Becquerel & Sievert Co., Ltd., Taipei (TW)

( * ) Notice: Subject to any disclaimer, the term of this patent is extended or adjusted under 35 U.S.C. 154(b) by 482 days.

(21) Appl. No.: 11/258,015

(22) Filed: Oct. 26, 2005

(65) Prior Publication Data

US 2007/0090305 A1 Apr. 26, 2007

(51) Int. Cl.
*G21F 5/018* (2006.01)
*A61M 36/08* (2006.01)

(52) U.S. Cl. ............... 250/506.1; 250/505.1; 250/515.1

(58) Field of Classification Search .............. 250/505.1, 250/506.1, 515.1; 220/758, 759; 294/28; *G21F 5/018; A61M 36/08*
See application file for complete search history.

(56) References Cited

U.S. PATENT DOCUMENTS

| | | | | |
|---|---|---|---|---|
| 4,144,461 | A * | 3/1979 | Glasser et al. | 250/506.1 |
| 4,511,167 | A * | 4/1985 | Kawaguchi | 294/28 |
| 5,433,339 | A * | 7/1995 | Sarver | 220/756 |
| 6,812,475 | B1 * | 11/2004 | Huang | 250/507.1 |
| 7,028,837 | B2 * | 4/2006 | Yanke et al. | 206/364 |
| 2006/0086909 | A1 * | 4/2006 | Schaber | 250/506.1 |

* cited by examiner

*Primary Examiner*—David A. Vanore
*Assistant Examiner*—Michael Maskell
(74) *Attorney, Agent, or Firm*—Troxell Law Office, PLLC

(57) ABSTRACT

The present invention provides an improved positron radioactive drug radiation shielding device, which achieves savings in space required to store a canister after dismantling the device. Furthermore, a tungsten sleeve is disposed within the canister, and functions in coordination with a syringe. The tungsten sleeve is able to block radioactive radiation released by radioactive drugs contained in the syringe. Moreover, a front cover and a rear cover joined to two sides of the canister enable a hermetically-sealed space to be formed within the canister, which increases the effectiveness of blocking the amount of radiation from the canister, thereby reducing danger to the human body from the radiation.

1 Claim, 10 Drawing Sheets

POSITRON RADIOACTIVE DRUG RADIATION SHIELDING DEVICE

BACKGROUND OF THE INVENTION (a) Field of the Invention

The present invention provides a dismountable shielding device that is easy to store and reduces space needed to store the device, and more particularly the present invention increases effectiveness of blocking radiation, and facilitates a syringe to extract drugs.

(b) Description of the Prior Art

Referring to FIGS. 1 and 2, which show a conventional container A structured from a front cover A1, a canister A2 and a rear cover A3. A handle A4 is secured affixed to a side edge of the canister A2, which results in the container A occupying too much space when stored.

Furthermore, a containment space A5 defined within the canister A2 is used to dispose a syringe therein. When the syringe is being used to extract radioactive drugs, in order to block the radioactive radiation released by the drugs, the internal syringe must be removed together with the canister A2, which causes inconvenience in use.

Hence, the inventor of the present invention proposes to resolve and surmount existent technical difficulties to eliminate the aforementioned shortcomings in prior art.

SUMMARY OF THE INVENTION

The present invention provides an improved positron radioactive drug radiation shielding device, which apart from achieving savings in space required to store the device, moreover, the present invention increases effectiveness of blocking radiation.

To enable a further understanding of said objectives and the technological methods of the invention herein, brief description of the drawings is provided below followed by detailed description of the preferred embodiments.

DETAILED DESCRIPTION OF THE PREFERRED EMBODIMENTS

The present invention provides an improved positron radioactive drug radiation shielding device, which apart from achieving savings on storage space occupied; moreover, the present invention increases effectiveness to block radiation.

Figure 1:
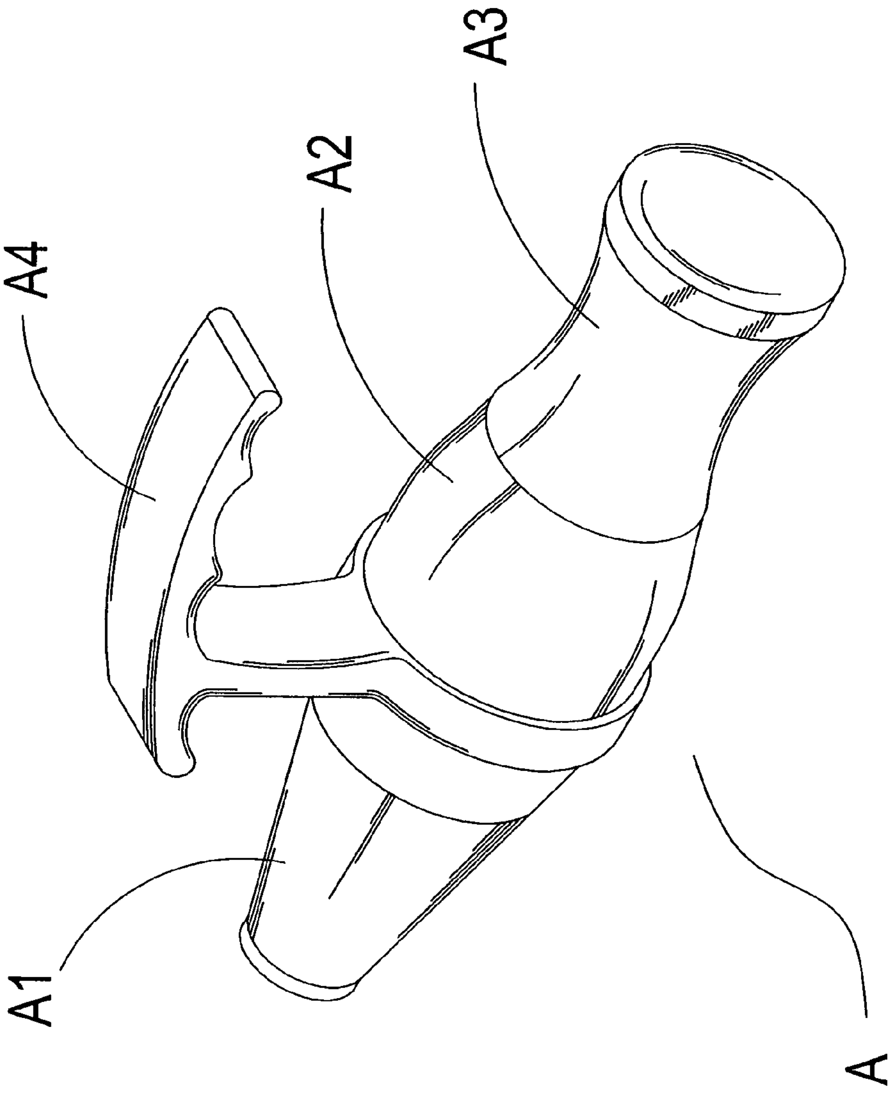
FIG.1 Prior Art
FIG. 1 shows an elevational view of prior art.
Figure 2:
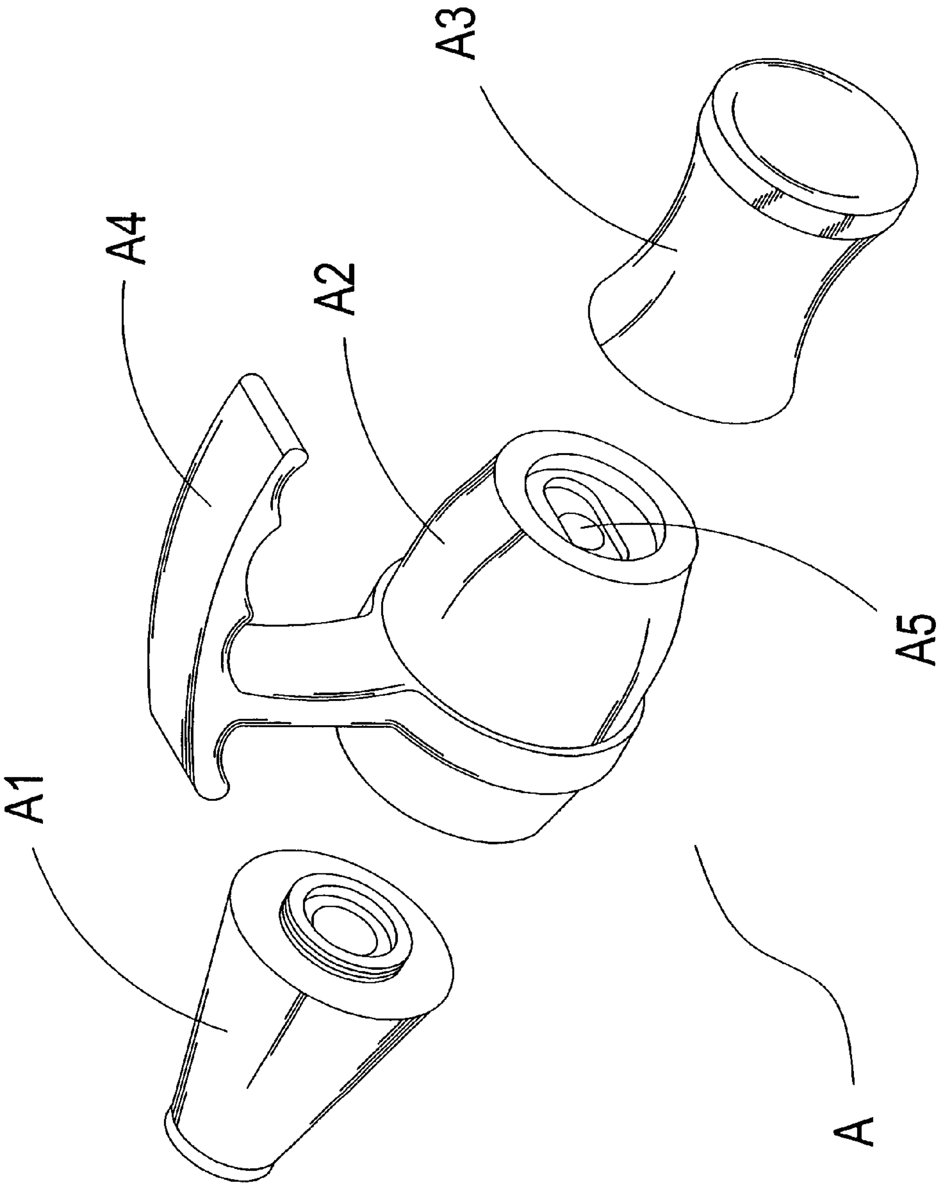
FIG.2 Prior Art
FIG. 2 shows an exploded elevational view of prior art.
Figure 3:
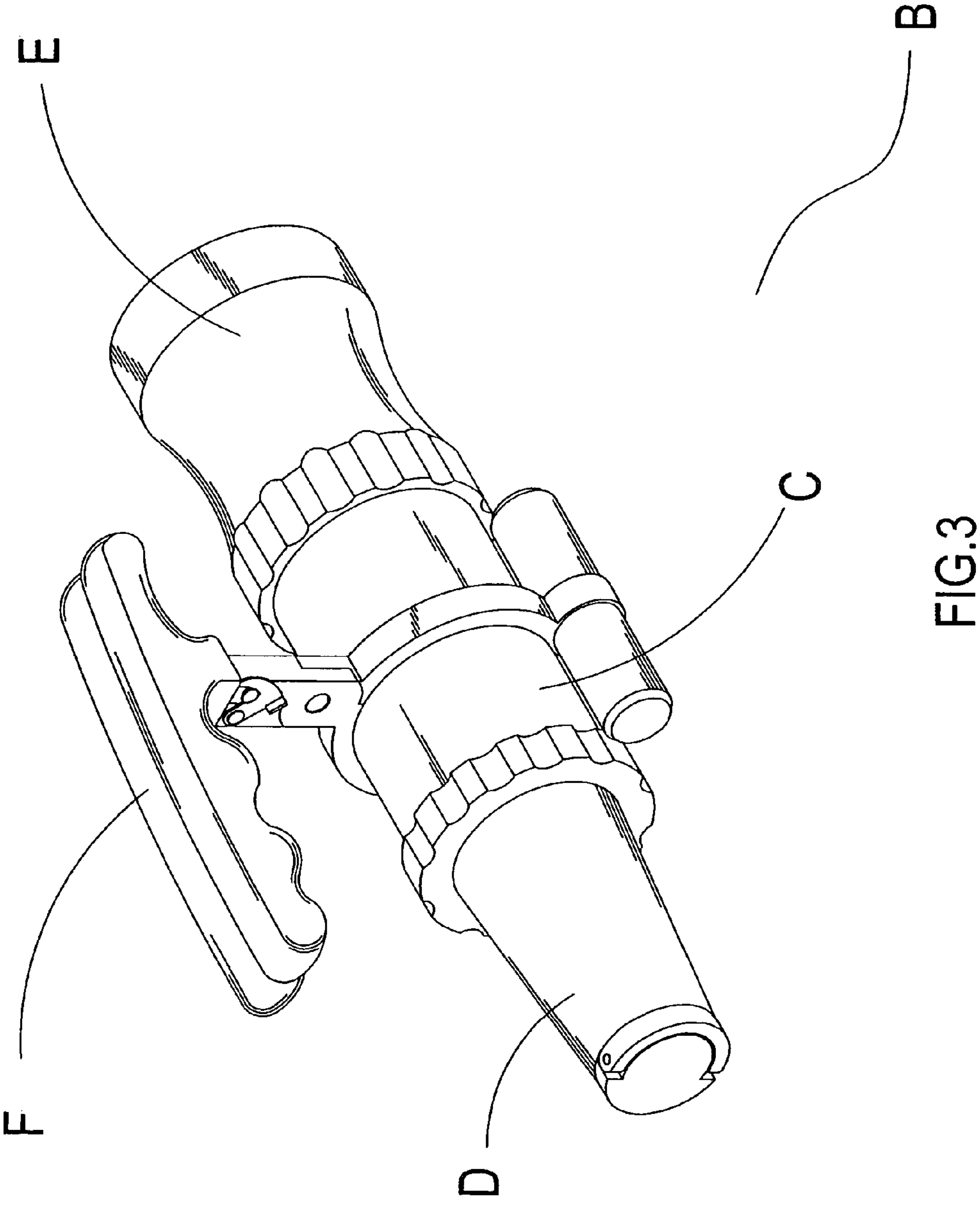
FIG. 3 shows an elevational view according to the present invention.
Figure 4:
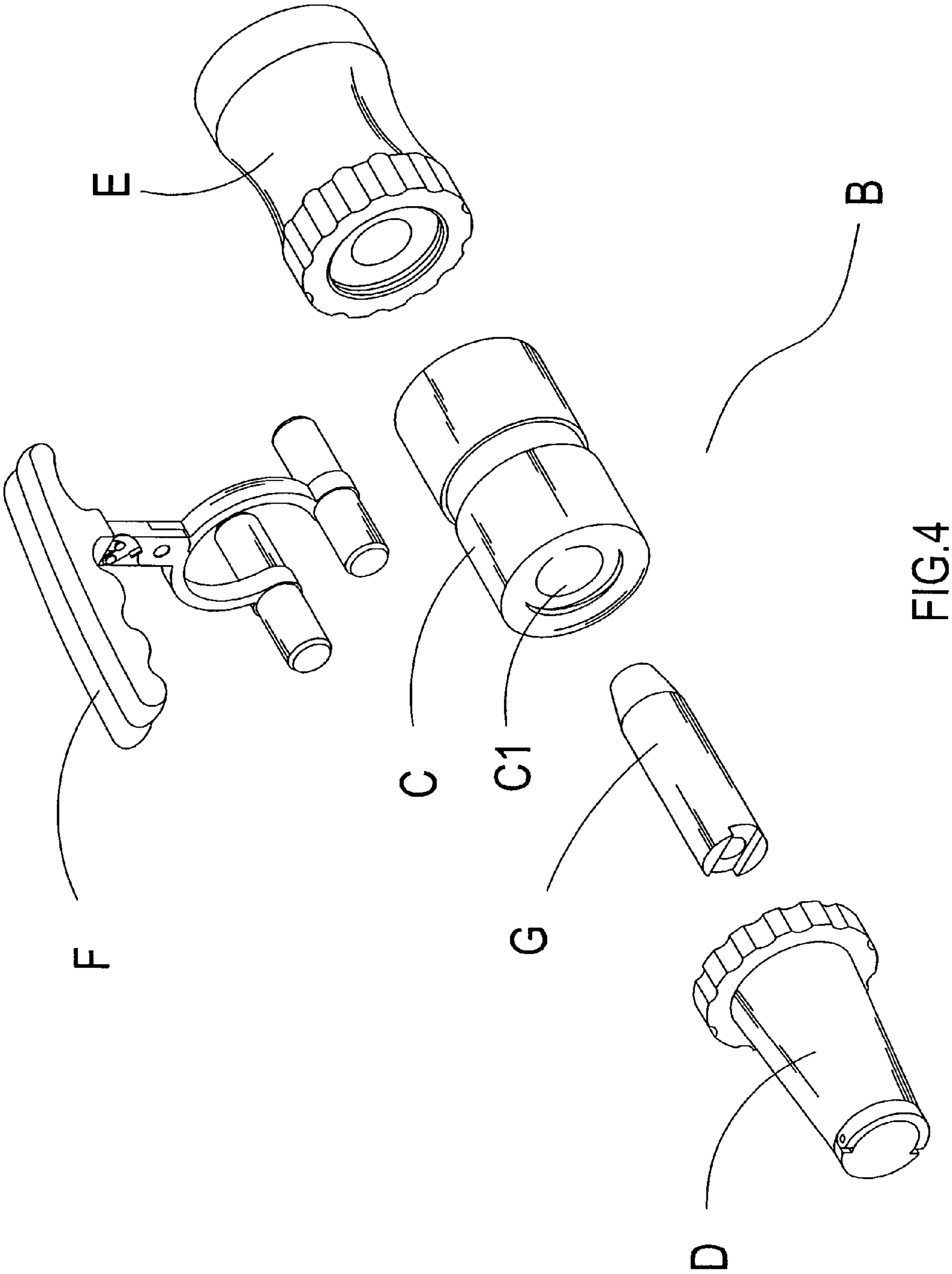
FIG. 4 shows an exploded elevational view according to the present invention.

Referring to FIGS. 3 and 4, in order to save on storage space, a clamp F is connected to an outer surface of a canister C of a shielding device B of the present invention. The clamp F is a movable device that can be detached from the outer surface of the canister C. Hence, savings on storage space are achieved when storing the canister C by merely first detaching the clamp F.

In order to increase effectiveness of blocking radioactive radiation, a containment space C1 is defined within the canister C of the shielding device B, which provides for a tungsten sleeve G to be disposed therein. A syringe containing radioactive drugs is disposed within the tungsten sleeve G, and the radiation produced by the radioactive drugs is effectively blocked by the tungsten sleeve G. A front cover D and a rear cover E are further joined to two sides of the canister C, thereby forming a hermetically-sealed space within the canister C, which further increases effectiveness to block radiation. Furthermore, when wanting to use the syringe to extract drugs, the tungsten sleeve G along with the syringe is merely pulled out from the canister C and moved to the position of a drug canister, whereupon the syringe can be used to extract the drugs, which is able to aid a user in his work.

Figure 5:
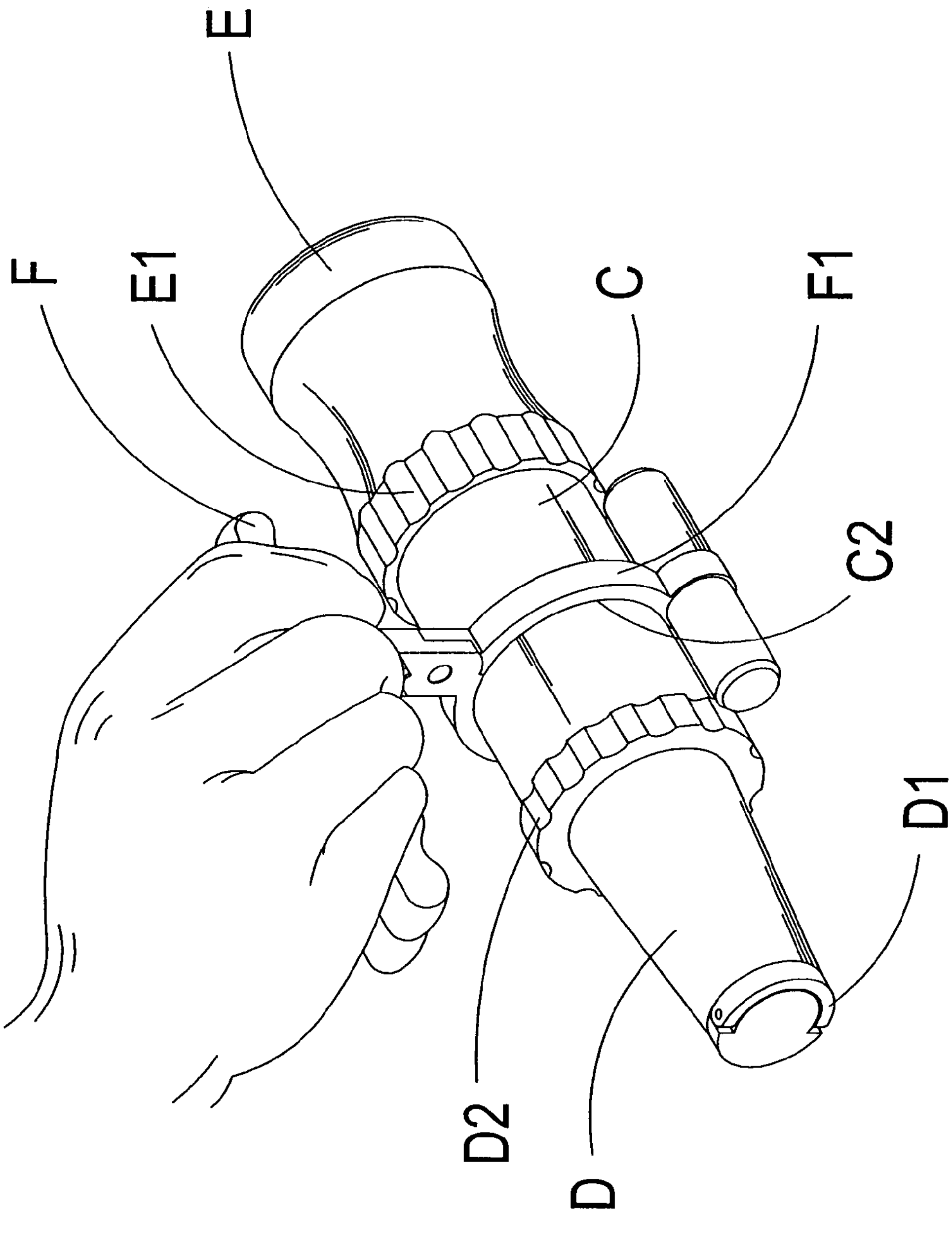
FIG. 5 shows a schematic view of an embodiment according to the present invention (1).
Figure 6:
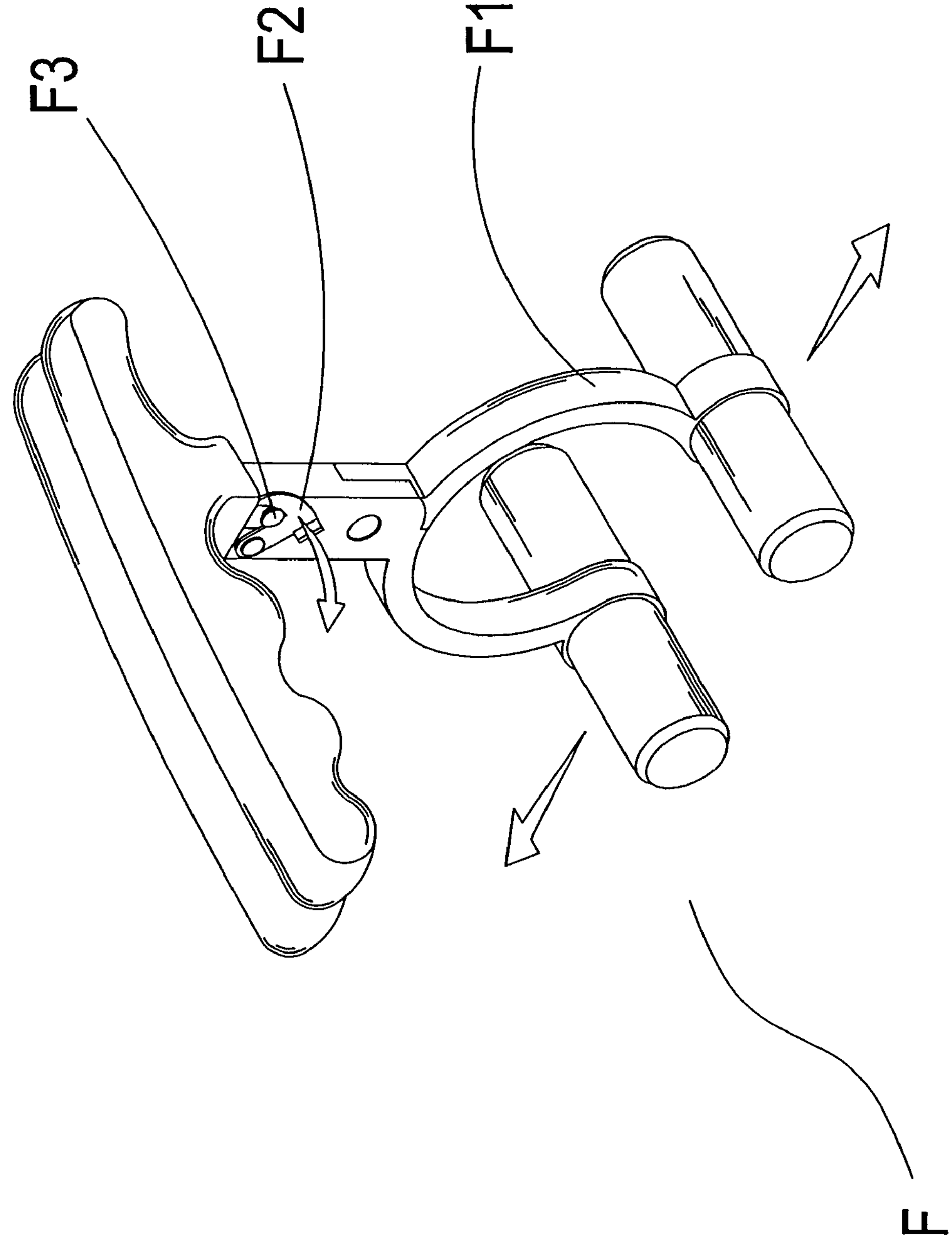
FIG. 6 shows a schematic view of the embodiment according to the present invention (2).

Referring to FIGS. 5 and 6, which show an embodiment of the improved positron radioactive drug radiation shielding device of the present invention, wherein the front cover D and the rear cover E are respectively joined to the two sides of the canister C, moreover, a plurality of indents D2, E1 encircle end outer edges of the front cover D and the rear cover E respectively, and a retaining ring D1 is disposed on an end of the front cover D. A groove C2 is defined on an outer surface of the canister C, which provides for the clamp F to clamp therein. A hook F2 and a protruding body F3 are configured on one end of a clamp support F1 of the clamp F. The clamp F is joined to the canister C by means of the hook F2 hooking onto the protruding body F3, which enables the clamp support F1 to tightly clamp within the groove C2, thereby providing a utility that facilitates the user to move and transport the shielding device B.

Figure 7:
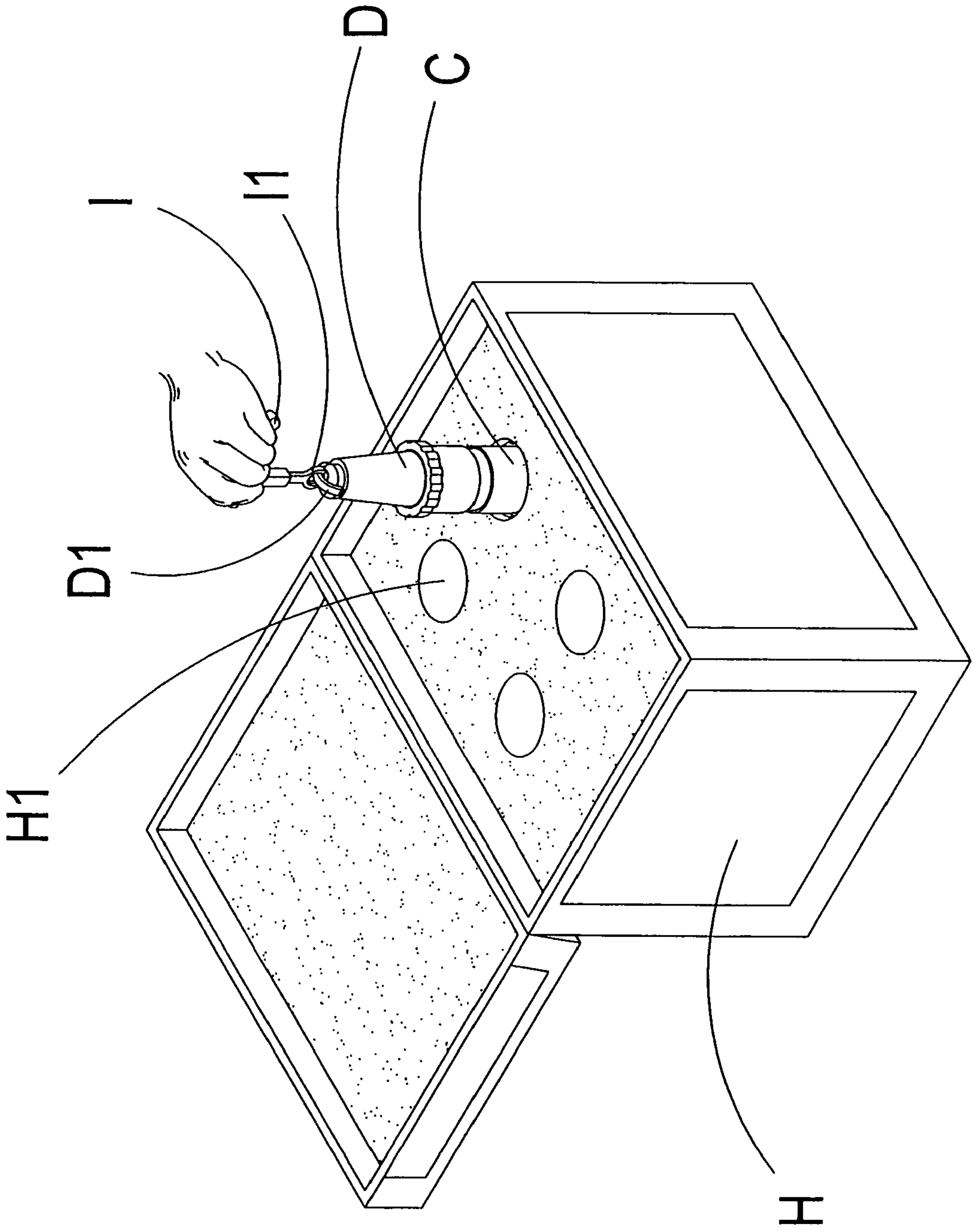
FIG. 7 shows a schematic view of an embodiment according to the present invention (3).
Figure 8:
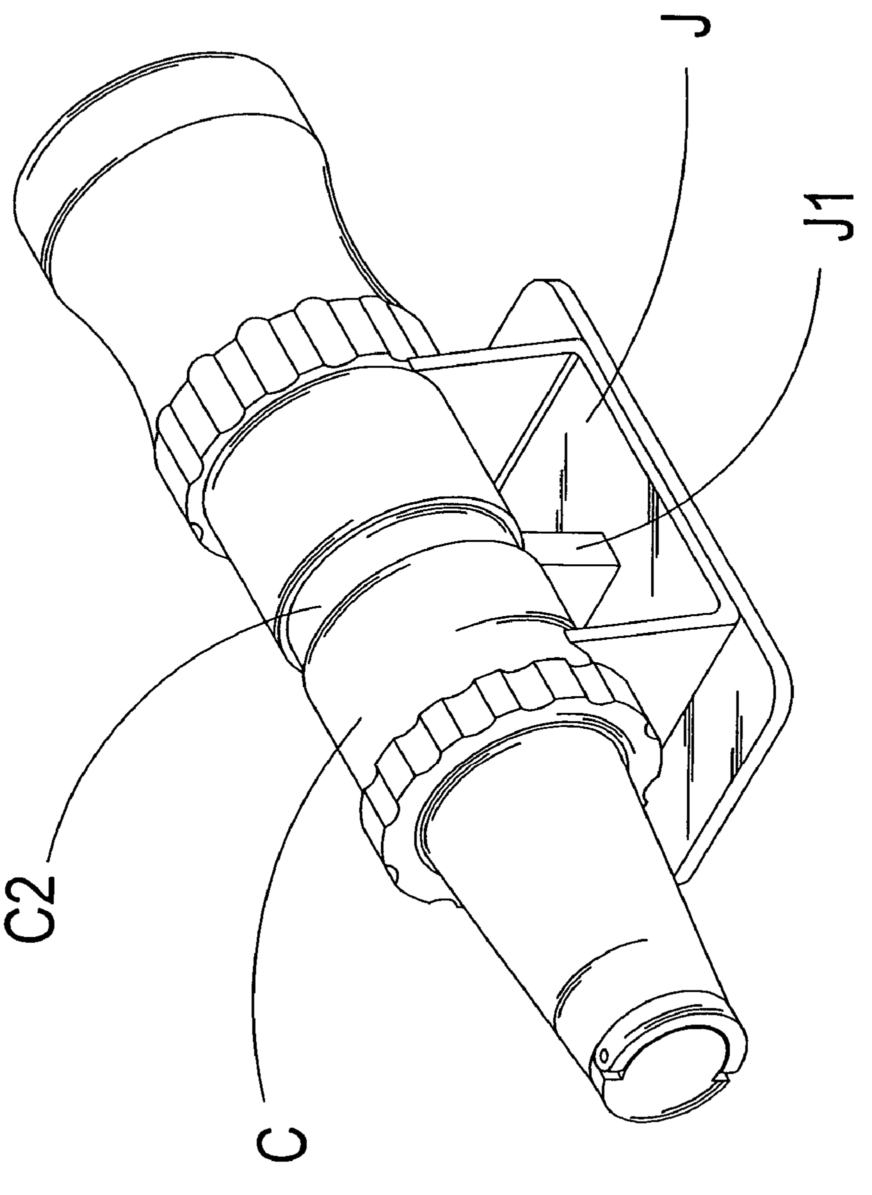
FIG. 8 shows a schematic view of an embodiment according to the present invention (4).

Referring to FIG. 7, a hook ring I1 of a hook I is used to hook the retaining ring D1 of the end of the front cover D, thereby facilitating the user to store the canister C in a storage space H1 within a box H. Referring to FIG. 8, the canister C is disposed on a securing base J, and is correspondingly joined within the groove C2 of the canister C by means of a catch strip J1 of the securing base J, thereby supporting the canister C on the securing base J in a stable disposition.

Figure 9:
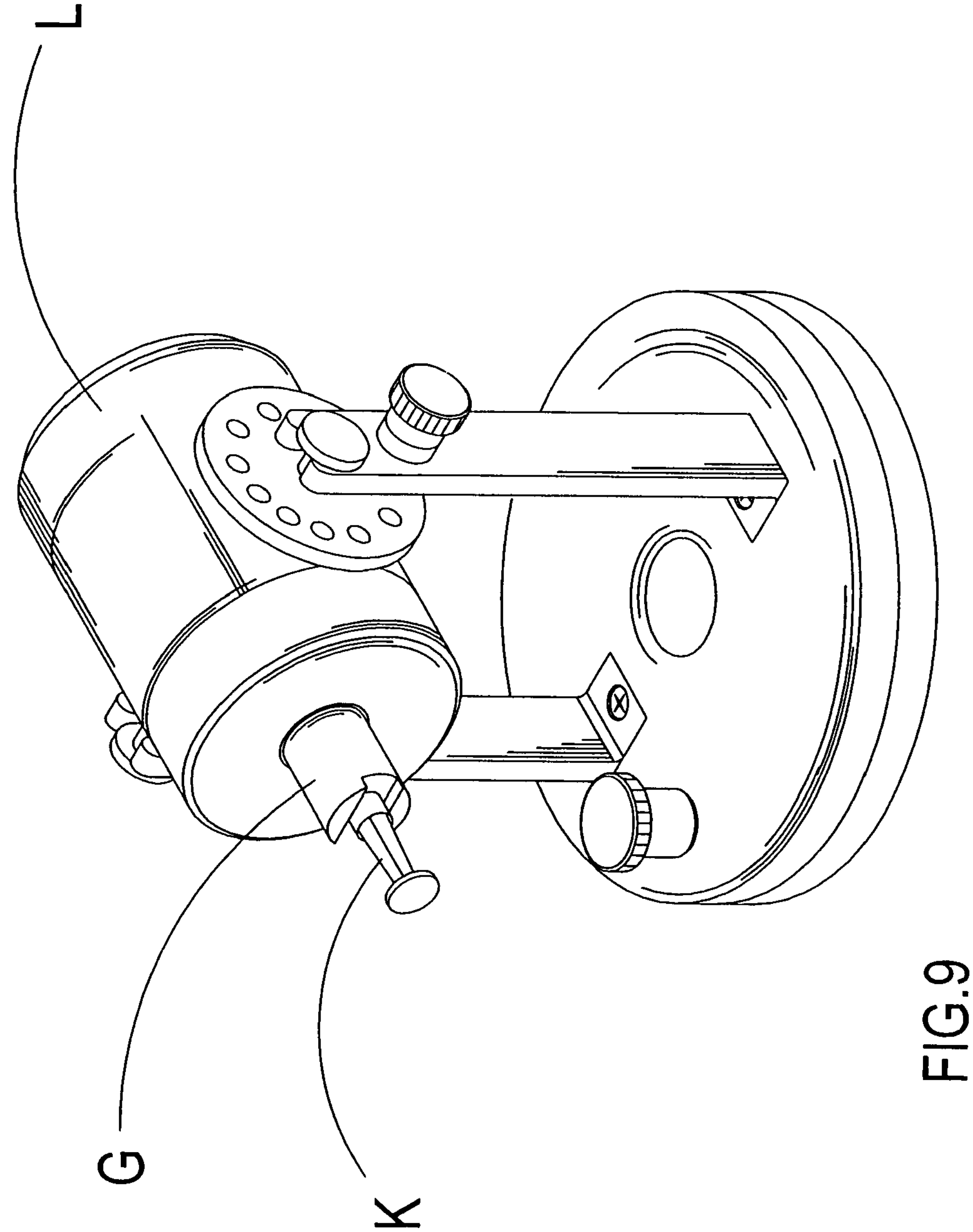
FIG. 9 shows a schematic view of an embodiment according to the present invention (5).
Figure 10:
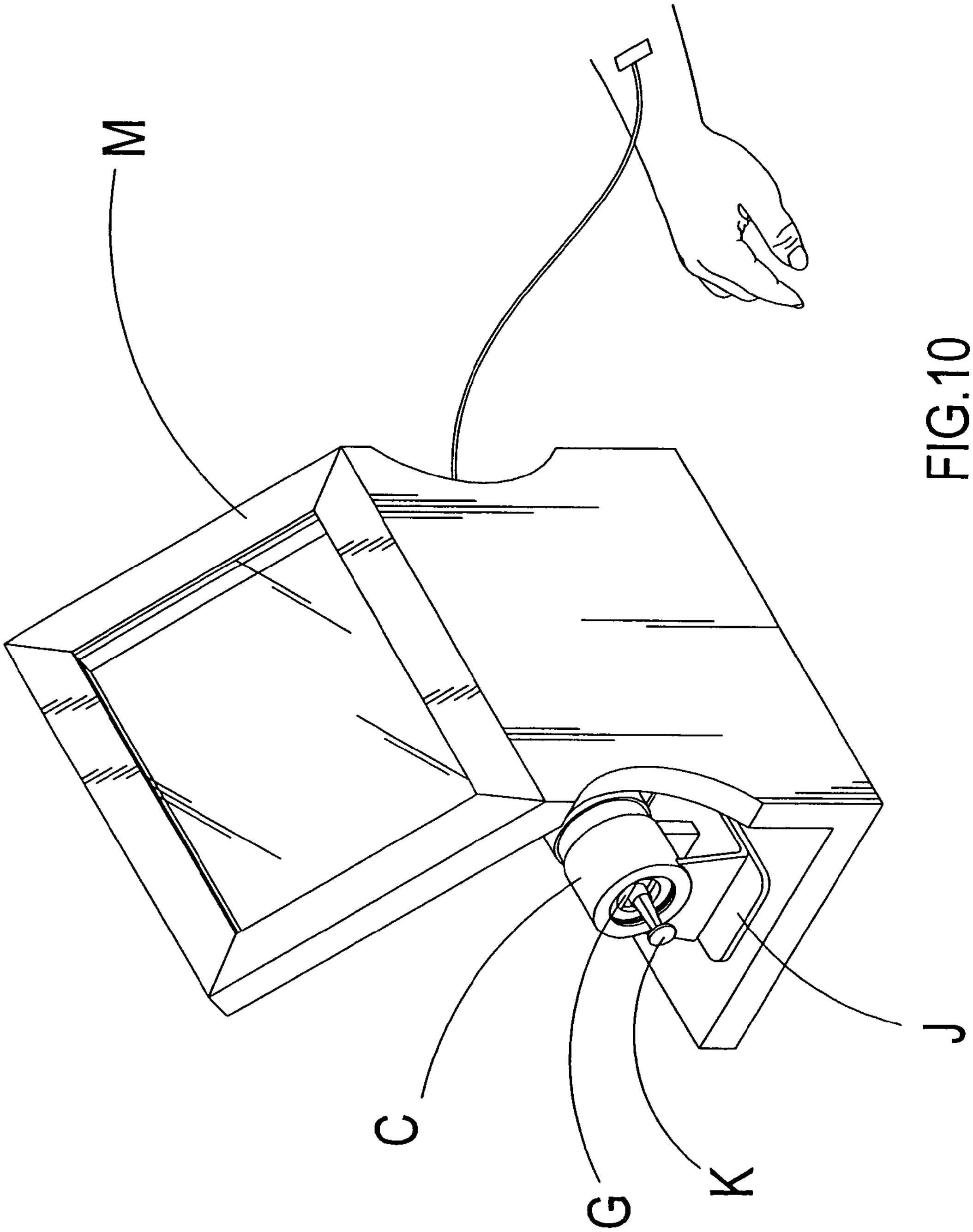
FIG. 10 shows a schematic view of an embodiment according to the present invention (6).

Referring to FIG. 9, which shows the tungsten sleeve G together with a syringe K inserted within a drug canister L packed with radioactive drugs, which facilitates the action of extracting the drugs with the syringe K. Furthermore, referring to FIG. 10, which shows the securing base J disposed on an operating platform M and the canister C disposed on the securing base J. After extracting the drugs, the syringe K and the tungsten sleeve G are inserted into the canister C for use by the user to inject the drugs.

In order to better explicitly disclose advancement and practicability of the present invention, a comparison with prior art is described hereinafter:

Shortcomings of Prior Art:

1. The handle is non-detachable, which results in wastage of storage space.

2. Operation is finicky when extracting drugs with the syringe,

Advantages of the Present Invention:

1. The clamp F is detachable from the canister C, thereby saving on space needed to store the present invention.

2. When wanting to use the syringe to extract drugs, the tungsten sleeve G together with the syringe K are merely withdrawn from the present invention to enable extraction of drugs to be carried out.

3. The tungsten sleeve G is disposed within the canister C, thereby increasing effectiveness of blocking radiation.

4. Provided with practicability and advancement.

5. Has increased commercial competitiveness.

In conclusion, the present invention in overcoming structural shortcomings of prior art has assuredly achieved effectiveness of anticipated advancement, and, moreover, is easily understood by persons unfamiliar with related art. Furthermore, contents of the present invention have not been publicly disclosed prior to this application, and practicability and advancement of the present invention clearly comply with essential elements as required for a new patent application. Accordingly, a new patent application is proposed herein.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. A positron radioactive drug radiation shielding device, comprising a front cover, a canister, a rear cover, a tungsten sleeve and a clamp; and is characterized in that a containment space is defined within the canister, which provides for the tungsten sleeve to be disposed therein; the tungsten sleeve provides for a syringe containing radioactive drugs to be disposed therein, moreover, the tungsten sleeve functions in unison with the syringe for removal and to extract drugs, and is able to further block radiation released from the drugs; the front cover and the rear cover joined to two sides of the canister enable a hermetically-sealed space to be formed within the canister, which further increases effectiveness of blocking radiation; a groove is defined on an outer surface of the canister, which provides for a clamp support of the clamp to clamp therein, a hook groove defined on the clamp is configured to pivot to selectively hook onto a protruding body, thereby enabling the clamp to clamp onto the canister, thereby facilitating a user to move and transport the positron radioactive drug radiation shielding device, moreover, after removing the clamp, savings are made on space needed to store the canister; furthermore, a retaining ring is disposed on an outer end of the front cover, which provides for a hook to hook the retaining ring for storing and lifting of the canister when sealed.

* * * * *